US010617346B2

(12) United States Patent
Scott

(10) Patent No.: US 10,617,346 B2
(45) Date of Patent: Apr. 14, 2020

(54) REMOTE ANESTHESIA MONITORING

(71) Applicant: Justin C. Scott, Sandy Springs, GA (US)

(72) Inventor: Justin C. Scott, Sandy Springs, GA (US)

( * ) Notice: Subject to any disclaimer, the term of this patent is extended or adjusted under 35 U.S.C. 154(b) by 266 days.

(21) Appl. No.: 15/106,928

(22) PCT Filed: Dec. 23, 2014

(86) PCT No.: PCT/US2014/072201
§ 371 (c)(1),
(2) Date: Jun. 21, 2016

(87) PCT Pub. No.: WO2015/100347
PCT Pub. Date: Jul. 2, 2015

(65) Prior Publication Data
US 2017/0000412 A1    Jan. 5, 2017

Related U.S. Application Data

(60) Provisional application No. 61/919,954, filed on Dec. 23, 2013.

(51) Int. Cl.
*A61B 5/00* (2006.01)
*G06F 19/00* (2018.01)
(Continued)

(52) U.S. Cl.
CPC .......... *A61B 5/4821* (2013.01); *A61B 5/0004* (2013.01); *A61B 5/02055* (2013.01); *A61B 5/742* (2013.01); *G06F 19/3418* (2013.01); *G06F 19/3481* (2013.01); *G16H 40/20* (2018.01); *A61B 5/021* (2013.01); *A61B 5/0245* (2013.01); *A61B 5/0488* (2013.01); *A61B 5/0816* (2013.01); *A61B 5/14542* (2013.01)

(58) Field of Classification Search
CPC combination set(s) only.
See application file for complete search history.

(56) References Cited

U.S. PATENT DOCUMENTS 5,544,661 A    8/1996  Davis et al.
6,364,834 B1   4/2002  Reuss et al.
(Continued)

OTHER PUBLICATIONS

Cone, et al., "Case Report of Remote Anesthetic Monitoring Using Telemedicine", Case Report, Anesth Analg 2004, 98:386-8.
(Continued)

*Primary Examiner* — Maroun P Kanaan
(74) *Attorney, Agent, or Firm* — Thomas | Horstemeyer, LLP

(57) ABSTRACT

Disclosed are various embodiments for remote anesthesia monitoring. For example, anesthesia status information may be automatically collected from the operating room and delivered to a specialized application executed by the anesthesiologist's mobile device. This allows for increased patient safety as the current model depends on the nurse anesthetist or physician assistant to call the supervising anesthesiologist when a problem is perceived. Through the use of remote monitoring, both the medical doctor and the anesthetist are now intimately involved in patient care, as compared to current situations where the medical doctor may be only peripherally involved.

20 Claims, 9 Drawing Sheets

(51) Int. Cl.
*G16H 40/20* (2018.01)
*A61B 5/0205* (2006.01)
*A61B 5/021* (2006.01)
*A61B 5/0245* (2006.01)
*A61B 5/0488* (2006.01)
*A61B 5/08* (2006.01)
*A61B 5/145* (2006.01)

(56) References Cited

U.S. PATENT DOCUMENTS

| | | | |
|---|---|---|---|
| 8,454,507 | B2 | 6/2013 | Tremper et al. |
| 2006/0206011 | A1 | 9/2006 | Higgins et al. |
| 2006/0288095 | A1* | 12/2006 | Torok .................. G06Q 10/08 709/223 |
| 2007/0156624 | A1* | 7/2007 | Palma ................ A61B 5/02455 706/60 |
| 2010/0305970 | A1 | 12/2010 | McLaren et al. |
| 2010/0306858 | A1 | 12/2010 | Mclaren et al. |
| 2011/0137134 | A1 | 6/2011 | Hemmerling et al. |
| 2013/0045685 | A1 | 2/2013 | Kiani |
| 2013/0110547 | A1* | 5/2013 | Englund .............. G16H 10/60 705/3 |
| 2013/0124227 | A1* | 5/2013 | Ellis .................... G06Q 50/22 705/3 |
| 2014/0180711 | A1* | 6/2014 | Kamen ................ G06Q 10/06 705/2 |
| 2015/0081338 | A1* | 3/2015 | Lai ..................... G06Q 50/22 705/3 |

OTHER PUBLICATIONS

Nurse-Anesthesia, "Premier Anesthesia Develops "tele-anesthesia" Program", Published on Nov. 26, 2011, 4 pages, http://www.nurse-anesthesia.org/content.php/277-Premier-Anesthesia-Develops-tele-anesthesia-Program.

Business Wire, "Anesthesia Business Consultants Shares Thoughts From the Advanced Institute for Anesthesia Practice Management: Securing Anesthesiology's Future, and Safeguarding its Present", Published on Apr. 14, 2014, 3 pages, http://www.businesswire.com/news/home/20140414006133/en/Anesthesia-Business-Consultants-Shares-Thoughts-Advanced-Institute#.U2D8ieZdWgR.

Rose, "McGill team helps pioneer remote anesthesia", The Globe and Mail, Published Sep. 10, 2010, 7 pages, http://www.theglobeandmail.com/life/health-and-fitness/mcgill-team-helps-pioneer-remote-anesthesia/article1379819/.

News Medical, Life Sciences and Medicine, "Tele-anesthesia can make OR care more efficient", Published on Apr. 9, 2013, 3 pages, http://www.news-medical.net/news/20130409/Tele-anesthesia-can-make-OR-care-more-efficient.aspx.

Kalorama Information, "Advanced Remote Patient Monitoring Systems, 6th Edition", Mar. 28, 2013, 15 pages, http://www.kaloramainformation.com/Advanced-Remote-Patient-7450566/.

Supplementary European Search Report for EP 14 87 3702 dated Jun. 7, 2017.

International Search Report dated Jun. 29, 2015.

European Communication Pursuant to Article 94(3) EPC for Application No. 14 873 702.6-1126 dated Mar. 21, 2018.

* cited by examiner

REMOTE ANESTHESIA MONITORING

CROSS-REFERENCE TO RELATED APPLICATIONS

This application is the 35 U.S.C. § 371 national stage application of PCT Application No. PCT/US2014/072201, filed Dec. 23, 2014, which claims priority to, and the benefit of, U.S. Provisional Application 61/919,954, entitled, "REMOTE ANESTHESIA MONITORING", and filed on Dec. 23, 2013, which is incorporated herein by reference in its entirety.

BACKGROUND

Anesthesia refers to a pharmacologically induced and reversible state of amnesia, analgesia, loss of responsiveness, loss of skeletal muscle reflexes, decreased stress response, or all of these simultaneously. Anesthesia may be administered in a hospital or other medical facility by physicians specializing in anesthesiology, known as anesthesiologists. In the United States, anesthesiologists usually complete four years of undergraduate education, four years of medical school, and four years of postgraduate medical training, or residency. In some cases, anesthesia may be administered by nurse anesthetists or physician assistants, who do not have the same level of training as anesthesiologists. For example, nurse anesthetists and physician assistants may have only completed four years of undergraduate education and two years of graduate training. In many states, nurse anesthetists and physician assistants are required to be supervised by physicians in administering anesthesia.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
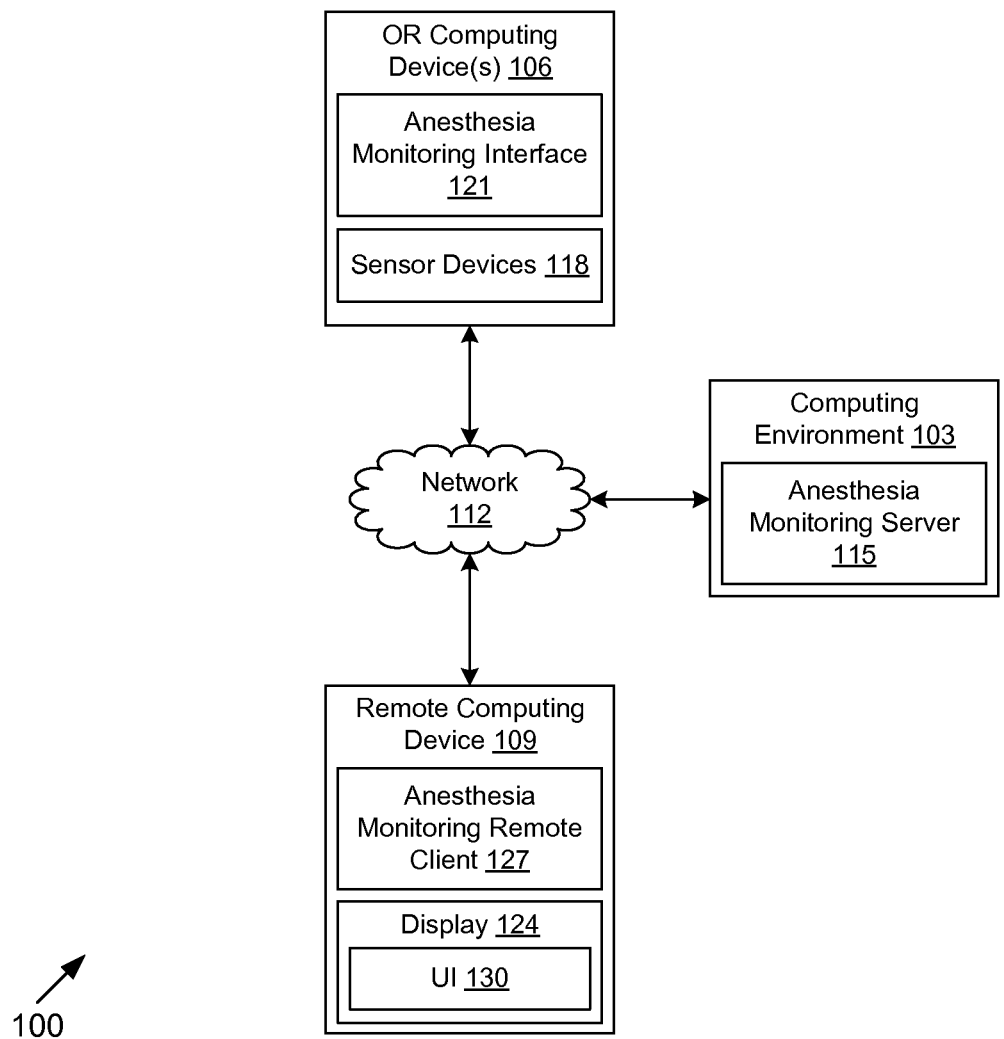
FIG. 1 is a schematic block diagram of a networked environment according to various embodiments of the present disclosure.

The present disclosure relates to remote anesthesia monitoring. As permitted by law, anesthesia may be administered by nurse anesthetists or physician assistants working under the supervision of anesthesiologists. For example, an anesthesiologist may start anesthesia for one patient and then move to other patients. In some cases, a single anesthesiologist may supervise anesthesia for four or more different patients, who may each undergo surgical procedures lasting hours. While the anesthesiologist is attending to other patients, a nurse anesthetist or a physician assistant may monitor the patient and maintain anesthesia. If the nurse anesthetist or physician assistant notices anything abnormal during the course of the anesthesia, the nurse anesthetist or physician assistant may page or call the anesthesiologist for further assistance. In addition, the anesthesiologist may check on the status of the patient periodically.

Various embodiments of the present disclosure facilitate remote monitoring of anesthesia. For example, anesthesia status information may be automatically collected from the operating room and delivered to a specialized application executed by the anesthesiologist's mobile device. This allows for increased patient safety as the current model depends on the nurse anesthetist or physician assistant to call the supervising anesthesiologist when a problem is perceived. For example, under the current model, situations may arise where the anesthesiologist is performing an hourly check on a patient and observes that blood loss is now excessive or that the patient's blood pressure is at a dangerously low range. Such conditions may have been occurring for ten minutes or more without the anesthesiologist being notified simply because the anesthetist did not choose to call or did not have time to call.

In addition to facilitating closer supervision of anesthetists, various embodiments of the present disclosure may facilitate immediate notification of emergencies. For instance, a particular patient, when being woken up from anesthesia, may experience a laryngeal spasm. Under the current model, the anesthesiologist may have to wait for a frantic call from the anesthetist or surgeon in the room. The anesthesiologist would have to find out various information during the call, such as, for example, which room the patient is in, vital signs of the patient, and so on. It may be difficult to get such information during emergency situations. Thus, various embodiments of the present disclosure may facilitate real-time monitoring of the patient so that it is immediately clear to the anesthesiologist which room the patient is in, the patient's current vital signs, and so on.

As a consequence of embodiments of the present disclosure, greater credence may be given to the anesthesia care team model of an anesthetist being supervised by a medical doctor. Through the use of remote monitoring, both the medical doctor and the anesthetist are now intimately involved in patient care, as compared to current situations where the medical doctor may be only peripherally involved. Further, embodiments of the present disclosure may improve Medicare or other regulatory compliance of periodic patient status checks in the operating room. For example, reminders may be automatically sent when a status check is due for documentation purposes. In the following discussion, a general description of the system and its components is provided, followed by a discussion of the operation of the same.

With reference to FIG. 1, shown is a networked environment 100 according to various embodiments. The networked environment 100 includes a computing environment 103, one or more operating room (OR) computing devices 106, and one or more remote computing devices 109, which may be in data communication with each other via a network 112. The network 112 includes, for example, the Internet, intranets, extranets, wide area networks (WANs), local area networks (LANs), wired networks, wireless networks, cable networks, satellite networks, or other suitable networks, etc., or any combination of two or more such networks.

The computing environment 103 may comprise, for example, a server computer or any other system providing computing capability. Alternatively, the computing environment 103 may employ a plurality of computing devices that may be arranged, for example, in one or more server banks or computer banks or other arrangements. Such computing devices may be located in a single installation or may be distributed among many different geographical locations. For example, the computing environment 103 may include a plurality of computing devices that together may comprise a hosted or "cloud" computing resource, a grid computing resource, and/or any other distributed computing arrangement. In some cases, the computing environment 103 may correspond to an elastic computing resource where the allotted capacity of processing, network, storage, or other computing-related resources may vary over time.

Various applications and/or other functionality may be executed in the computing environment 103 according to various embodiments. Also, various data is stored in a data store that is accessible to the computing environment 103. The components executed on the computing environment 103, for example, include an anesthesia monitoring server 115, and other applications, services, processes, systems, engines, or functionality not discussed in detail herein. The anesthesia monitoring server 115 is executed to facilitate communication between the OR computing devices 106 and the remote computing devices 109. For example, the anesthesia monitoring server 115 may receive monitoring updates from the OR computing devices, potentially process those updates, and then provide monitoring information to the remote computing device 109. In some cases, the anesthesia monitoring server 115 may also facilitate remote control of the OR computing devices 106 by the remote computing devices 109. In addition, the anesthesia monitoring server 115 may store or have access to patient history records, lab result records, radiology records, cardiac testing records, and/or other pertinent records.

The OR computing devices 106 may comprise, for example, a server computer, a desktop computer, a mobile computer, or any other system providing computing capability. Specifically, the OR computing devices 106 may correspond to computing devices present in an operating room (OR) environment. The OR computing devices 106 may include sensor devices 118 that are configured to monitor and/or control various aspects of patient care in the OR environment. The sensor devices 118 may monitor, for example, blood pressure, heart rate with five or three-lead echocardiogram (ECG) tracing, body temperature, respiration rate, oxygen saturation, carbon dioxide, nitrous oxide or other anesthetic agents, electromyography (EMG) monitoring, and/or other patient parameters. In one embodiment, an OR computing device 106 may be configured to capture images of equipment that displays the patient vital signs, and these images may be transmitted to the anesthesia monitoring server 115 and/or the remote computing device 109. For example, a sensor device 118 may include a camera configured to capture readings from patient monitoring equipment in the OR. The images of the readings may be transmitted to the remote computing device 109, and/or the images may be processed, e.g., using optical character recognition, to obtain the readings from the images.

Various applications and/or other functionality may be executed in the OR computing devices 106 according to various embodiments. Also, various data is stored in a data store that is accessible to the OR computing devices 106. The components executed on the OR computing devices 106, for example, include an anesthesia monitoring interface 121, and other applications, services, processes, systems, engines, or functionality not discussed in detail herein. The anesthesia monitoring interface 121 is executed to receive and potentially process data from the sensor devices 118 and to communicate the results to the anesthesia monitoring server 115 and/or the remote computing device 109. In addition, the anesthesia monitoring interface 121 may receive commands from the remote computing device 109 (potentially by way of the anesthesia monitoring server 115).

The remote computing device 109 is representative of a plurality of client devices that may be coupled to the network 112. The remote computing device 109 may comprise, for example, a processor-based system such as a computer system. Such a computer system may be embodied in the form of a desktop computer, a laptop computer, personal digital assistants, cellular telephones, smartphones, set-top boxes, music players, web pads, tablet computer systems, game consoles, electronic book readers, or other devices with like capability. The remote computing device 109 may include a display 124. The display 124 may comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc.

The remote computing device 109 may be configured to execute various applications such as an anesthesia monitoring remote client 127 and/or other applications. The anesthesia monitoring remote client 127 may be executed in a remote computing device 109, for example, to access network content served up by the computing environment 103 and/or other servers, thereby rendering a user interface 130 on the display 124. To this end, the anesthesia monitoring remote client 127 may comprise, for example, a browser, a dedicated application, etc., and the user interface 130 may comprise a network page, an application screen, etc. The anesthesia monitoring remote client 127 may comprise a native application, a web-based application, a hybrid application, or another type of application. The remote computing device 109 may be configured to execute applications beyond the anesthesia monitoring remote client 127 such as, for example, code calculator applications, email applications, social networking applications, word processors, spreadsheets, and/or other applications.

Next, a general description of the operation of the various components of the networked environment 100 is provided. To begin, the anesthesia monitoring remote client 127 may be installed upon a remote computing device 109 of a physician or other supervisory user. The operating rooms of a medical facility are configured with OR computing devices 106 that are equipped to communicate with sensor devices 118. The anesthesia monitoring interface 121 may be configured to render instructions and/or other information on a display for the anesthetist or others in the room.

In one embodiment, the anesthesia monitoring server 115 manages the OR computing devices 106 in one or more medical facilities, and enables communication with the remote computing device 109. In another embodiment, the anesthesia monitoring remote client 127 may communicate directly with the OR computing devices 106. The OR computing devices 106 may be configured to output data in a variety of data formats, including extensible markup language (XML), health level 7 (HL7), and so on. The data may be provided by the OR computing devices 106 in a push or pull fashion. The OR computing devices 106 may execute commercially available medical device software such as CAPSULETECH SMARTLINX or other software. In some cases, the OR computing devices 106 may communicate with one or more intermediate servers that provide data or receive instructions from the anesthesia monitoring server 115 and/or the anesthesia monitoring remote client 127.

Security measures may be enabled to ensure regulatory compliance. For example, the physician user may be required to be authenticated via username, password, fingerprint, voice recognition, security keys, numerical codes, etc. In one embodiment, the remote computing device 109 may be "paired" with the OR computing device 106 by enabling a pairing function when both are in close proximity. Such pairing may be enabled by near field communication, Bluetooth®, audio communication, recognition of machine-readable fixed identifiers, and/or other technologies. The anesthesia monitoring server 115 (and/or the anesthesia monitoring interface 121 or the anesthesia monitoring remote client 127) may manage various preferences that may be categorized as medical facility preferences, physician preferences, and patient preferences. The anesthesia monitoring server 115 (and/or the anesthesia monitoring interface 121 or the anesthesia monitoring remote client 127) may also have access to medical records, lab records, and/or other patient history for the patients.

In various embodiments, the anesthesia monitoring remote client 127 may provide physician users the ability to view the ORs to which they are assigned. In some cases, the anesthesia monitoring server 115 may perform the initial assignment of patients to physician users. The assignments may be based upon expertise, surgeons involved, nature of the patient procedure, compensation, and/or other criteria. A physician user may be able to transfer assignments to other supervising physician users in cross-cover situations.

Surgeon preferences may be stored to provide optimally matched patient care. For example, a surgeon may indicate generally or for a particular case that he or she wants an arterial line, an epidural, a nerve block, certain medicines to be administered, and so on. The surgeon preferences may be surfaced to the physician users via the user interface 130.

The anesthesia monitoring remote client 127 may provide the ability to sign in for the start, finish, and hourly checks on the patient in order to pair with the medical record for compliance issues. In some embodiments, algorithms such as the advanced cardiac life support (ACLS) protocol may be accessed via the anesthesia monitoring remote client 127. In one embodiment, an emergency detected in one OR may cause an alarm to be generated on all remote computing devices 109 in a given area so that the nearest physician user can respond. Different screens and data points can be assigned different colors for ease of viewing and can be user customized. An optional calculator may be accessible. Pediatric dosing can be included automatically based upon the patient's weight.

In some embodiments, communication may be facilitated between the physician user at the remote computing device 109 and the anesthetist user at the OR computing device 106. For example, the physician user may issue instructions to the anesthetist user (e.g., give 100 units of Neo-Synephrine® to raise a low blood pressure reading), and/or the anesthetist user may respond with confirmations or questions. The communication may be via text, voice, video, a predefined interface, and/or other approaches.

In some embodiments, the anesthesia monitoring remote client 127 may facilitate remote control of various apparatuses coupled to the OR computing devices 106. Such apparatuses may facilitate dosing of various drugs to control blood pressure, anesthetic depth, etc. Such apparatuses may facilitate control of ventilator settings and/or other aspects of patient care.

For example, drugs could be connected to a delivery machine that communicates with the OR computing device 106 and is connected to a patient's intravenous (IV) line. The physician could select an element on a user interface 130 to initiate any of the following example interventions:

Low blood pressure (BP) and low heart rate (HR), give Ephedrine 10 mg.

Low BP and normal to high HR, give Neo-Synephrine® 100 mcg.

Vital signs trending upward, give a dose of a narcotic.

Patient attempting to breathe over the ventilator rate, give a dose of a muscle relaxant.

For long cases, re-dose an antibiotic at a specified time interval.

For an abrupt reaction to a surgical stimulus, give Propofol 50 mg.

The above drugs and other drugs may be set by the patient weight for pediatric dosing.

In some embodiments, the OR computing device 106 may be connected to the anesthesia machine, for example, to increase or decrease the vaporizer concentration delivered in response to the patient's reaction to surgical stimulus as indicated by change in vital signs, capnography, etc.; to increase or decrease $O_2$, $N_2O$, or air concentrations relative to $O_2$ saturation or anesthetic depth. In some embodiments, the OR computing device 106 may be connected to the ventilator to alter ventilator settings in relation to $CO_2$ capnography, surgeon preferences (e.g., neurosurgery cases may warrant low $CO_2$ concentrations, etc.), or in preparation of termination of the anesthetic and waking the patient up.

Figure 2A:
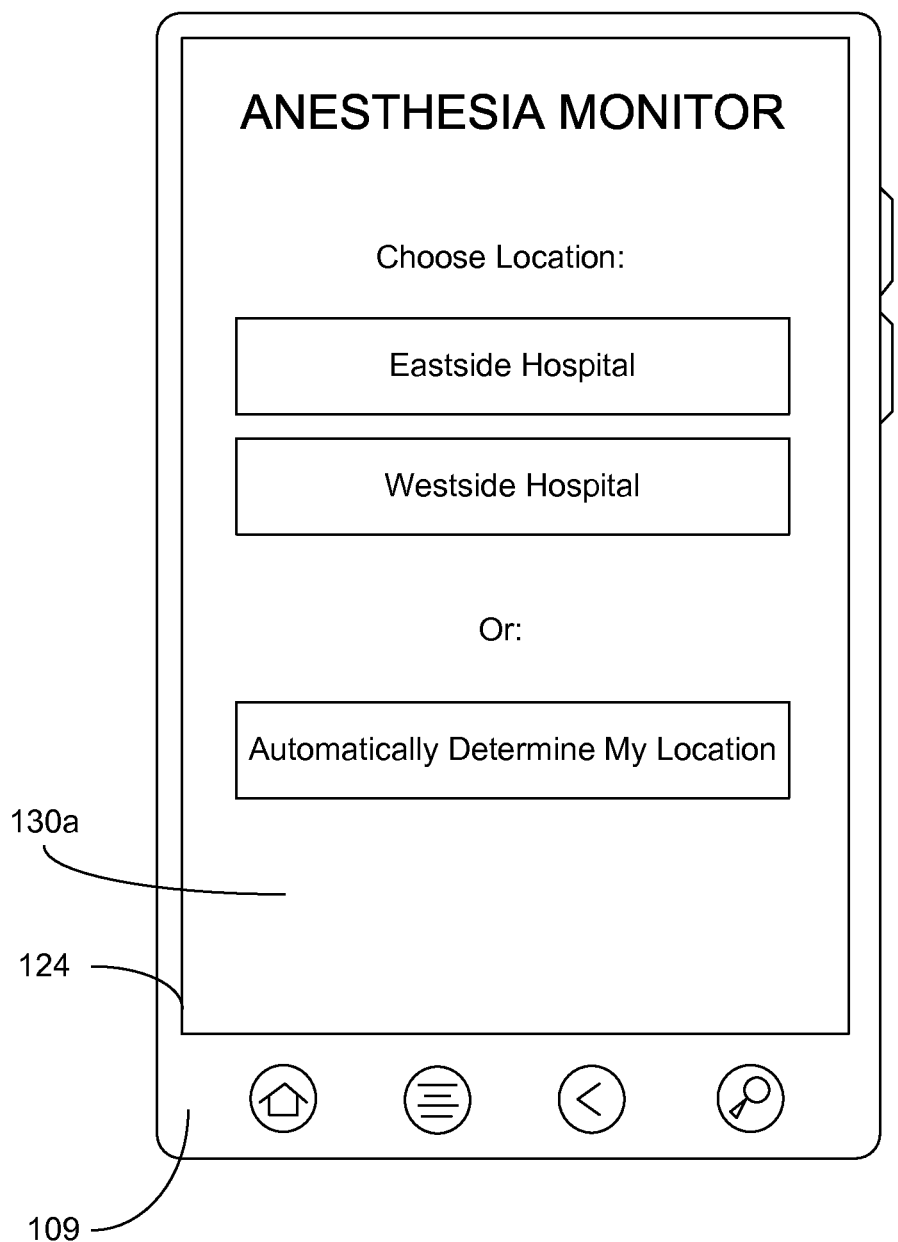
FIGS. 2A-2F are pictorial diagrams of example user interfaces rendered by a client in the networked environment of FIG. 1 according to various embodiments of the present disclosure.

Referring next to FIGS. 2A-2F, shown are pictorial diagrams of a sequence of example user interfaces 130a . . . 130f rendered by an anesthesia monitoring remote client 127 (FIG. 1) upon a display 124 of a remote computing device 109 in the networked environment 100 (FIG. 1) according to various embodiments of the present disclosure. It is noted that the background colors and/or background patterns of the user interfaces 130 may be user customizable. FIG. 2A shows a user interface 130a corresponding to a location-selection screen for the user to select a location (e.g., a hospital or other medical facility). Pre-configured locations (e.g., "Eastside Hospital" and "Westside Hospital") may be presented. In some embodiments, the user may select "automatically determine my location" to determine the location by way of a location-finding service available to the anesthesia monitoring remote client 127. Such services may include global positioning system (GPS), triangulation based upon cell towers, geolocation of network addresses, geolocation of Wi-Fi access points, and so on.

Figure 2B:
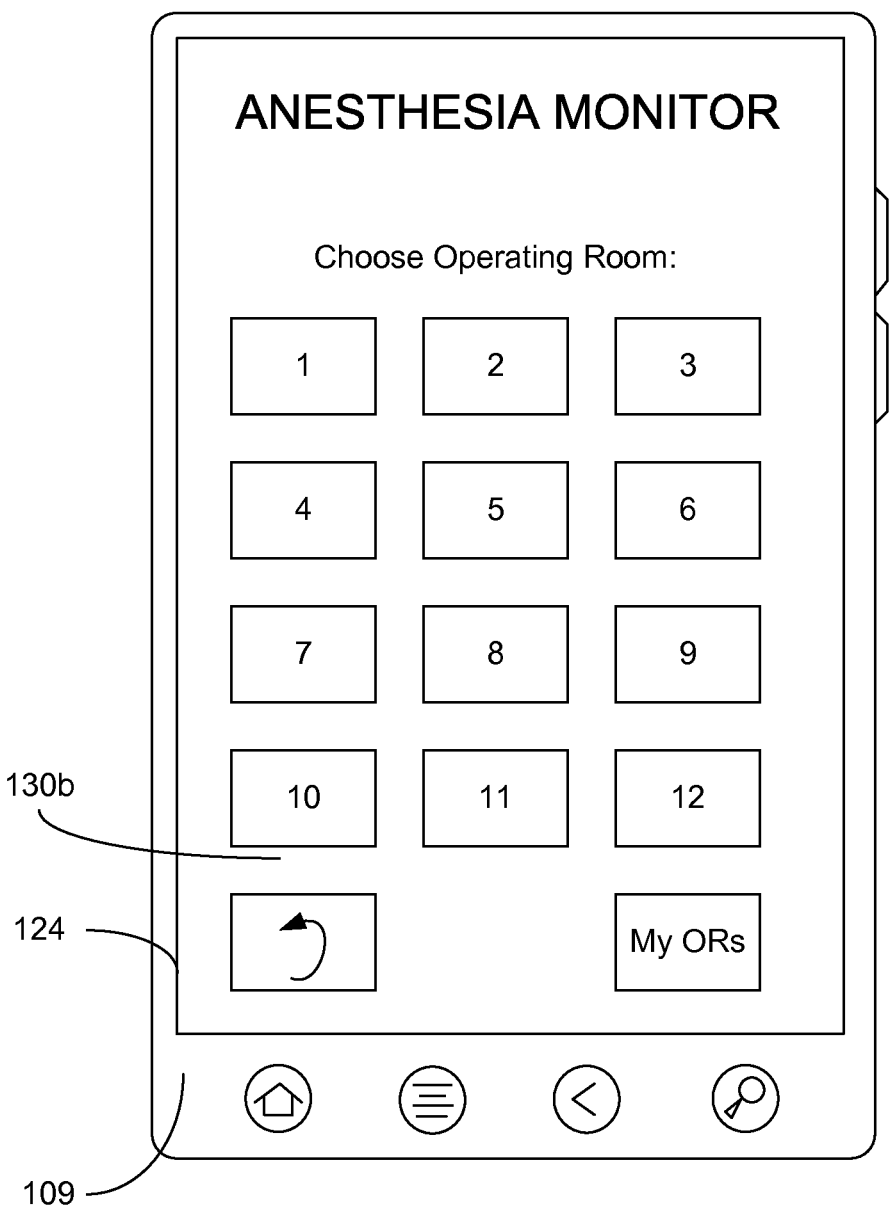

FIG. 2B shows a user interface 130b to allow selection from among multiple operating rooms at a given location. For example, different buttons or selection components may be shown for each room at the location. A component may be provided in order to return to the previous user interface 130a. A component may be provided in order to proceed to the next user interface 130c (FIG. 2C) ("My ORs"). In some cases, where fewer than a predetermined number of ORs are shown, the anesthesia monitoring remote client 127 may proceed immediately from the user interface 130a to the user interface 130c without an intermediate task of OR selection.

Figure 2C:
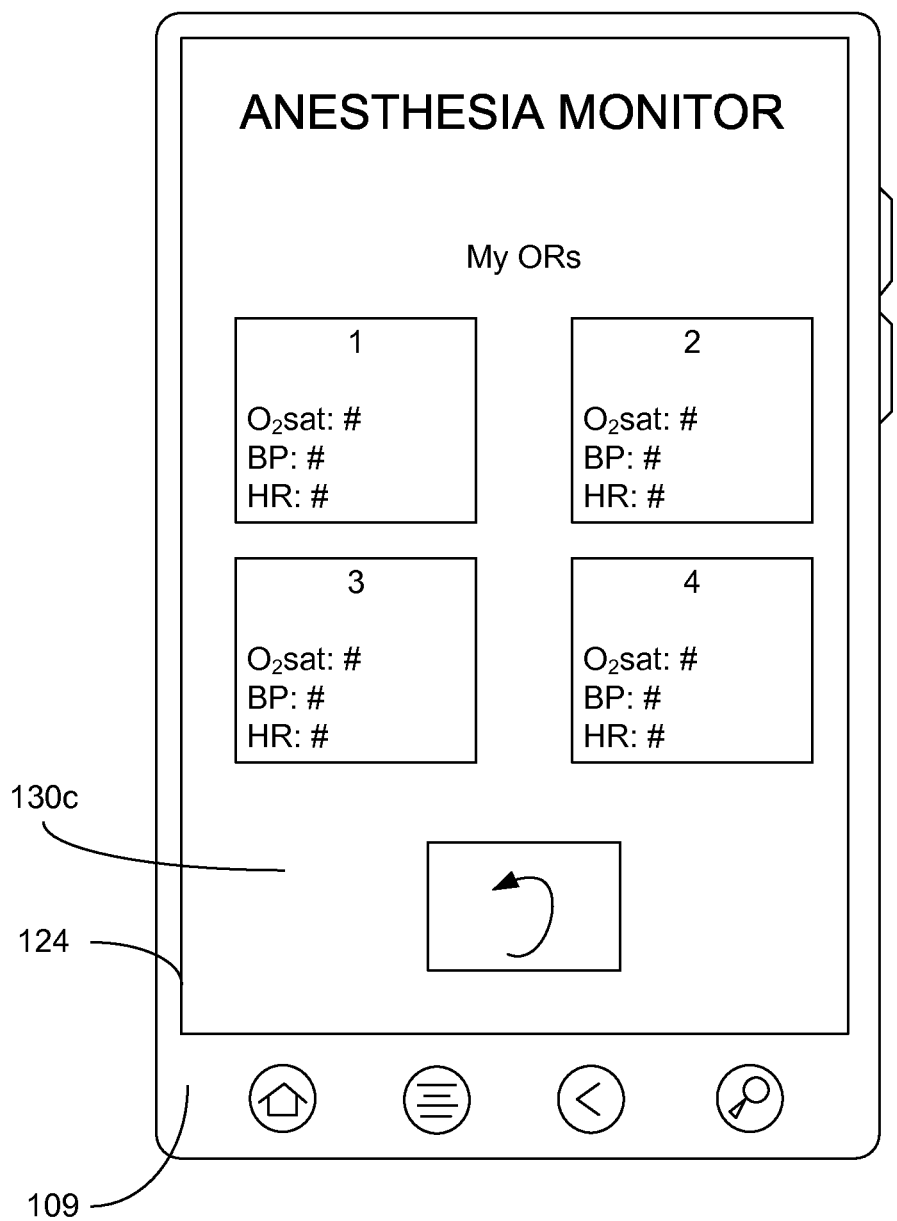

FIG. 2C shows a user interface 130c to allow selection from among a subset of the ORs shown in FIG. 2B. For example, the ORs shown in FIG. 2B may be the particular ones to which the physician is assigned at the current time.

Otherwise, the subset of the ORs may be preconfigured for the particular physician. In one embodiment, selection of an OR via the user interface 130b may cause the OR to be shown in the user interface 130c. For example, in the user interface 130b, the physician user may drag an OR component to the "My ORs" component, or the physician user may hold down an OR component for a given period of time via a long press. In some embodiments, the long press may trigger a vibration of the remote computing device 109. In the user interface 130c, a component may be provided in order to return to the previous user interface 130b. Alternatively, a gesture (e.g., swiping backward) may also return to the user interface 130b. Other forms of user interaction (e.g., voice recognition) may be used to navigate among user interfaces 130.

In FIG. 2C, the OR components may be colored or otherwise have indicia to show the status of the anesthesia in the corresponding OR. For example, the OR number may be green if everything is within tolerance, while the OR number may flash red if an issue occurs. In some examples, the components for selecting the ORs may display various vital signs, e.g., oxygen saturation, blood pressure, heart rate, etc., and/or other information. These may be a subset of those vital signs that are available via the next user interface 130, and they may be selected for display in the user interface 130c based upon whether they are within a threshold alarm range. In some cases, an audible alarm or vibration may be triggered by the anesthesia monitoring remote client 127 upon detection of an alarm. The physician user may be able to drag or otherwise select the OR components in order to remove them from the user interface 130c, e.g., when anesthesia has been completed or otherwise if supervision is no longer necessary. Various embodiments may provide notifications that the patient is in the room, that the patient is ready to be seen in pre-op, that the patient is about to wake up, and/or other notifications. In response to such notifications, a chime or other sound may be played and/or user interface components may change color, flash, and so on.

In some cases, user interface components relating to a particular OR may be color-coded to distinguish them from other ORs, each of which may utilize a distinct color scheme.

Figure 2D:
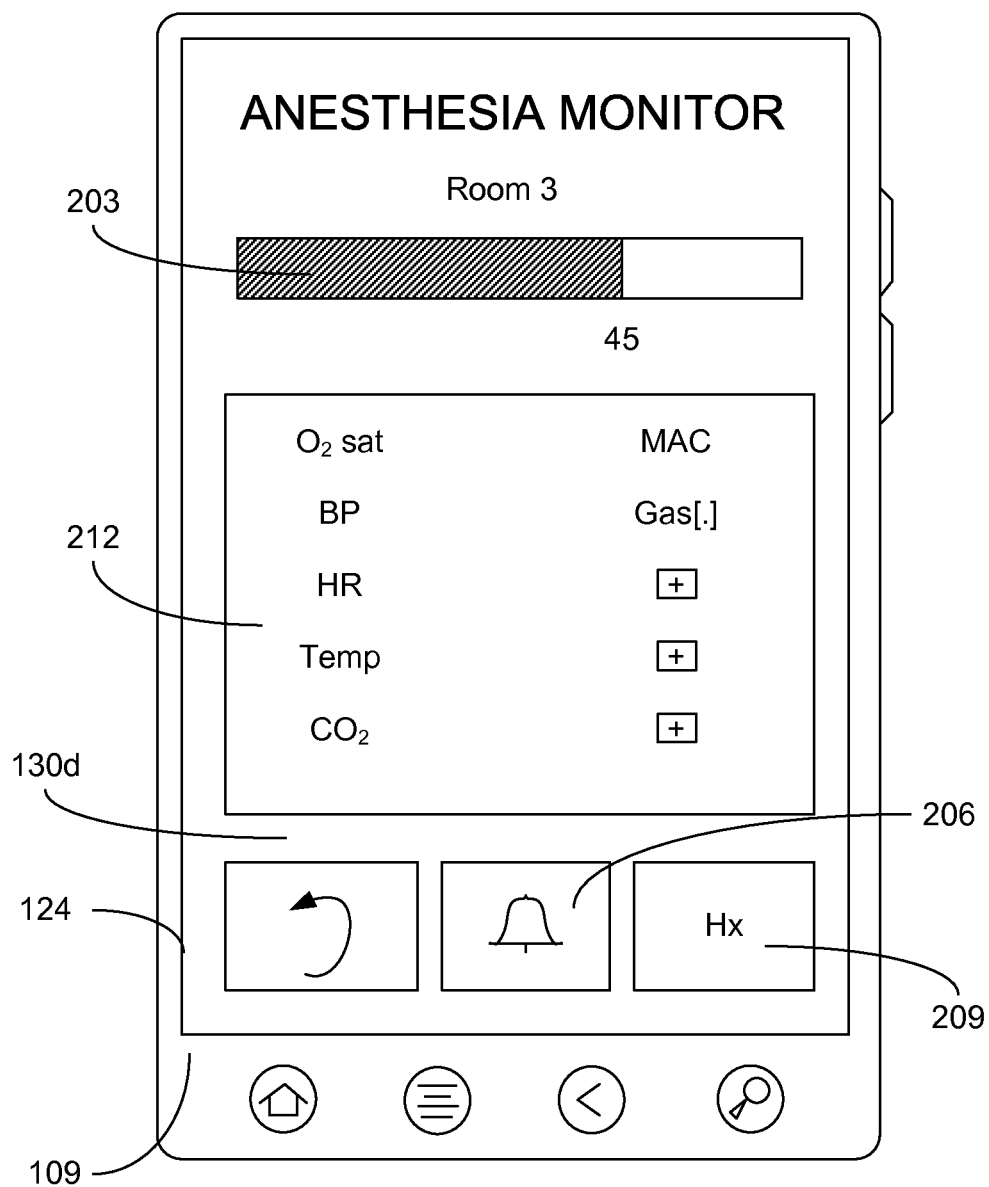

FIG. 2D shows a user interface 130d corresponding to a detail screen for a particular OR. A status bar 203 may visibly indicate the time remaining until the next scheduled assessment by the physician and/or the time since the previous assessment by the physician. In some embodiments, a countdown timer may be present in place of a status bar 203. A reset button or component may be used to reset the time remaining. Various data points for vital signs may be shown, including oxygen saturation, blood pressure, heart rate, temperature, carbon dioxide, end tidal carbon dioxide, and so on. In the user interface 130d, a component may be provided in order to return to the previous user interface 130c.

In one embodiment, the various data points may be provided in different colors. Each physician or medical facility may configure which data points are to be monitored. In one embodiment, an alarming data point may blink, flash, or change color. Alarms may be set at a desired interval, e.g., one minute. A component 206 may be provided to jump to a user interface 103f (FIG. 2F) for configuring alarms and limits, and a component 209 may be provided to jump to a user interface 103e (FIG. 2E) for viewing patient history and/or lab results. If an alarm occurs, in one embodiment, the physician user may tap anywhere inside the area 212, or another area, to acknowledge the alarm. Other gestures may be supported for acknowledging alarms.

Figure 2E:
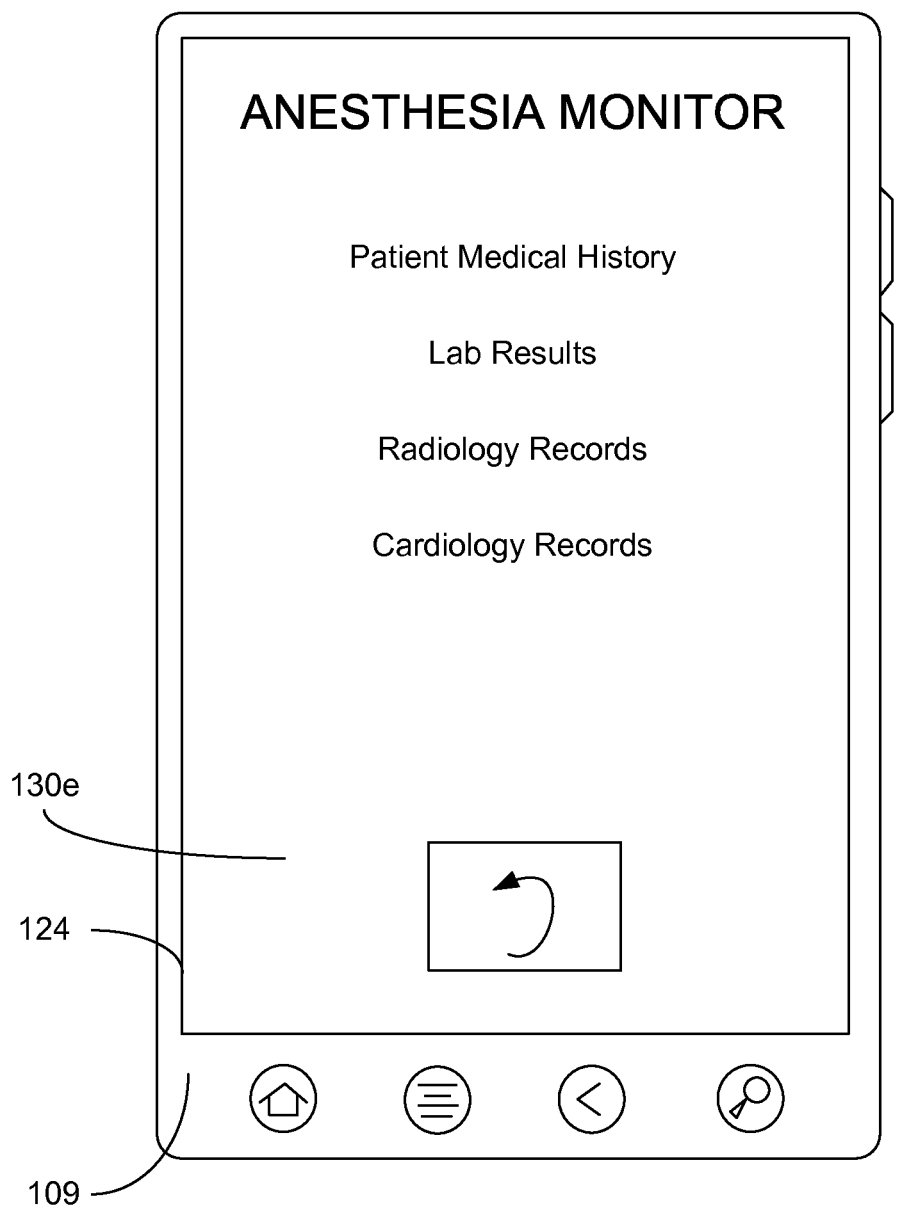

FIG. 2E shows a user interface 130e configured for viewing patient medical history, lab results, radiology records, cardiology records, and/or other pertinent records. In the user interface 130e, a component may be provided in order to return to the previous user interface 130d. The types of lab results may be selectable and/or preconfigured for the physician user, for the patient, and/or for the medical facility.

Figure 2F:
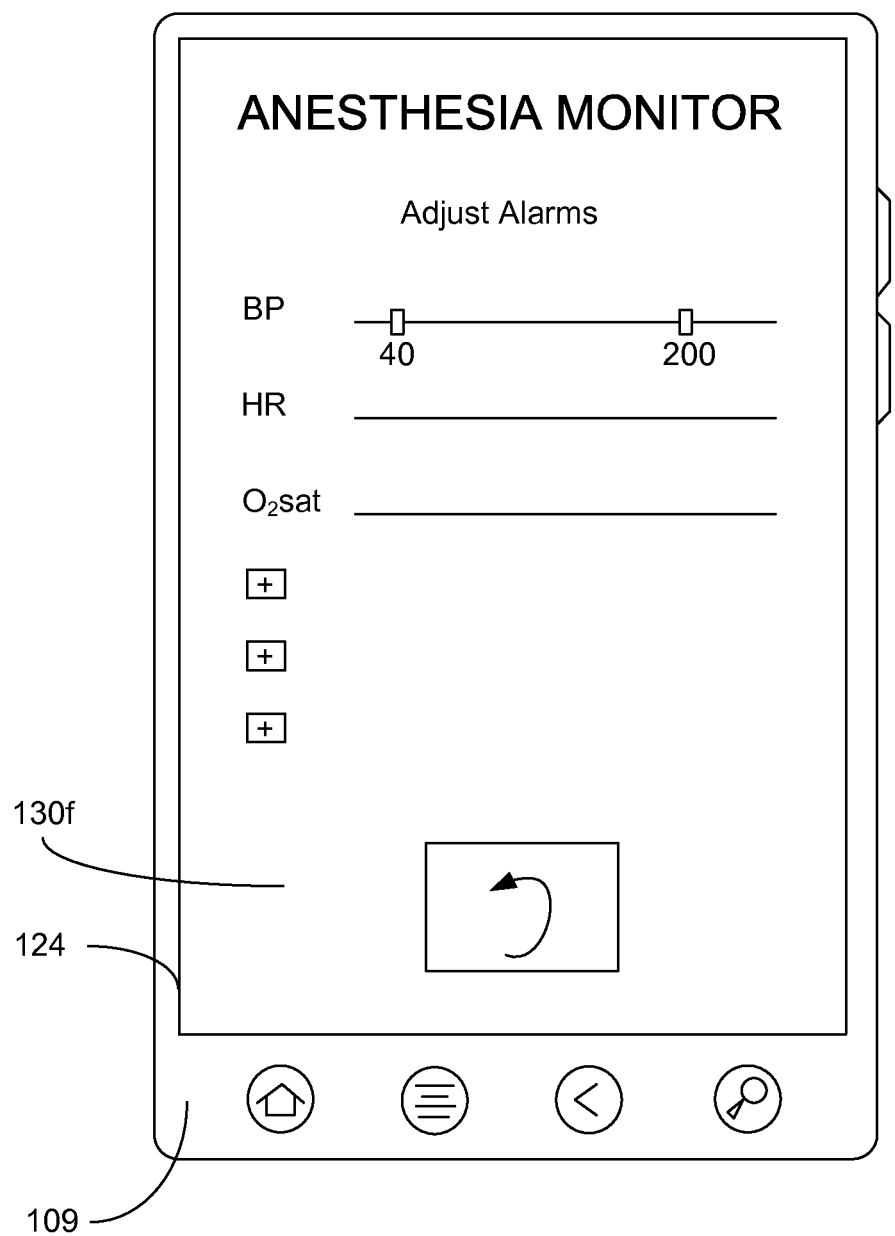

FIG. 2F shows a user interface 130f configured for setting alarms for various data points. In the user interface 130f, a component may be provided in order to return to the previous user interface 130d. For example, various sliders may be provided in order to establish low range and/or high range alarms. In addition, alarms may be configured based upon rate of change. It is noted that the alarms may be configured on a per-patient basis. For example, it may be normal and acceptable that a senior adult may have relatively high blood pressure. If their blood pressure is cut in half, they may not get as much cerebral flow and may have a bad outcome. However, the same blood pressure value for a younger individual may be acceptable. Thus, standard alarms for young and healthy adults may not be acceptable for the senior adult. In some cases, alarms may be automatically triggered when a reading deviates from a baseline reading by more than a threshold amount, e.g., 5%, 10%, 20%, etc.

Figure 3:
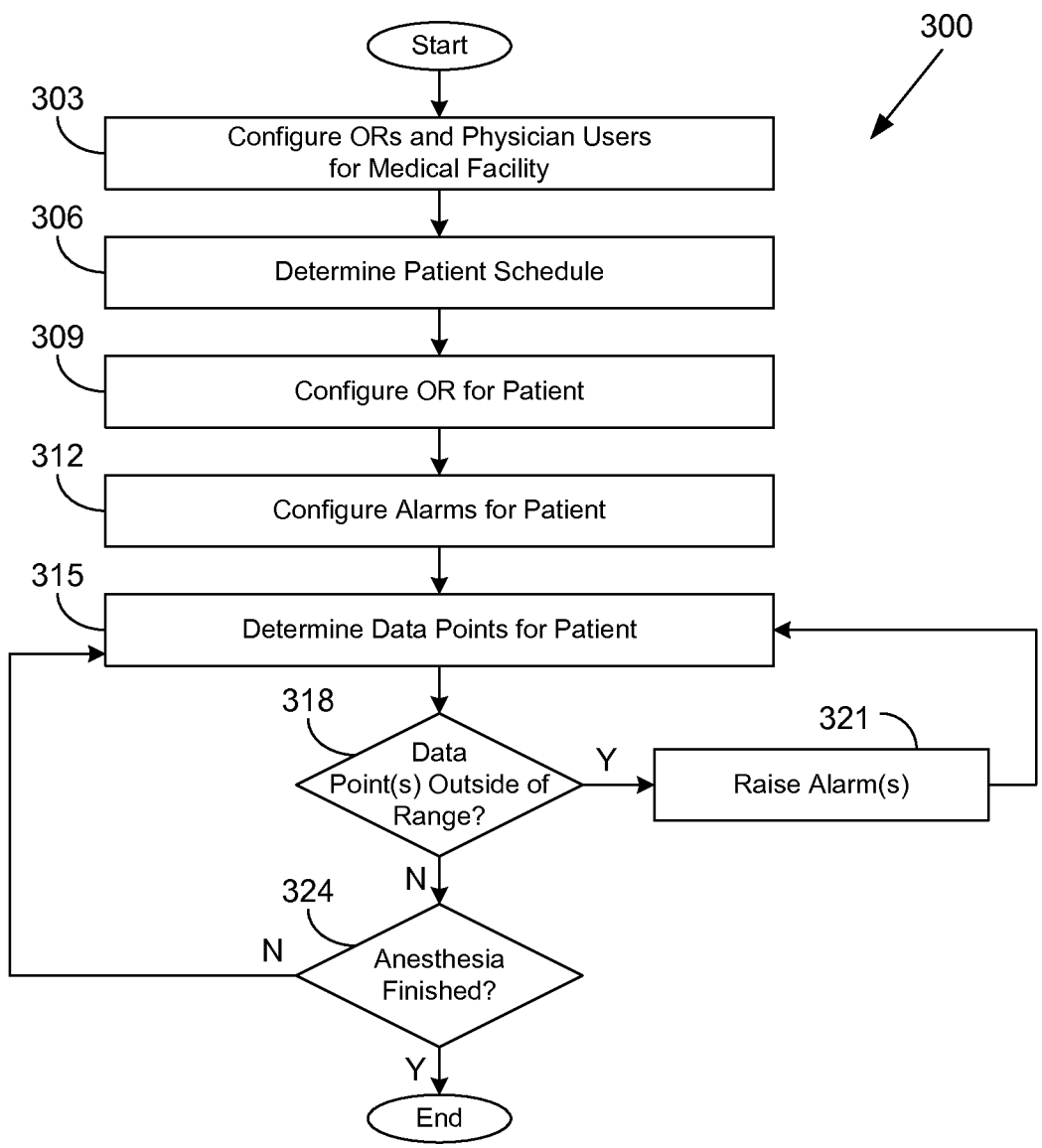
FIG. 3 is a flowchart illustrating one example of functionality implemented as portions of the networked environment of FIG. 1 according to various embodiments of the present disclosure.

Referring next to FIG. 3, shown is a flowchart 300 that provides one example of the operation of a portion of the networked environment 100 (FIG. 1) according to various embodiments. It is understood that the flowchart of FIG. 3 provides merely an example of the many different types of functional arrangements that may be employed to implement the operation of the portion of the networked environment 100 as described herein. As an alternative, the flowchart of FIG. 3 may be viewed as depicting an example of elements of a method implemented in the computing environment 103 (FIG. 1), the OR computing devices 106 (FIG. 1), and/or the remote computing device 109 (FIG. 1) according to one or more embodiments.

Beginning with box 303, the operating rooms and physician users are configured for a particular medical facility. In box 306, the patient schedule is determined. In box 309, a particular OR is configured for a patient. In box 312, alarms are configured for the patient. In box 315, anesthesia begins and data points are determined for the patient.

In box 318, it is determined whether the data points are outside of an acceptable range. If outside of the range, one or more alarms may be raised in box 321. The flowchart 300 may then return to box 315 and continue determining data points for the patient. If the data points are not outside of the range, the flowchart 300 may continue to box 324 and determine whether anesthesia for the patient is finished. If anesthesia is not finished, the flowchart 300 may return to box 315 and continue determining data points for the patient. If the anesthesia is finished, the flowchart ends.

Figure 4:
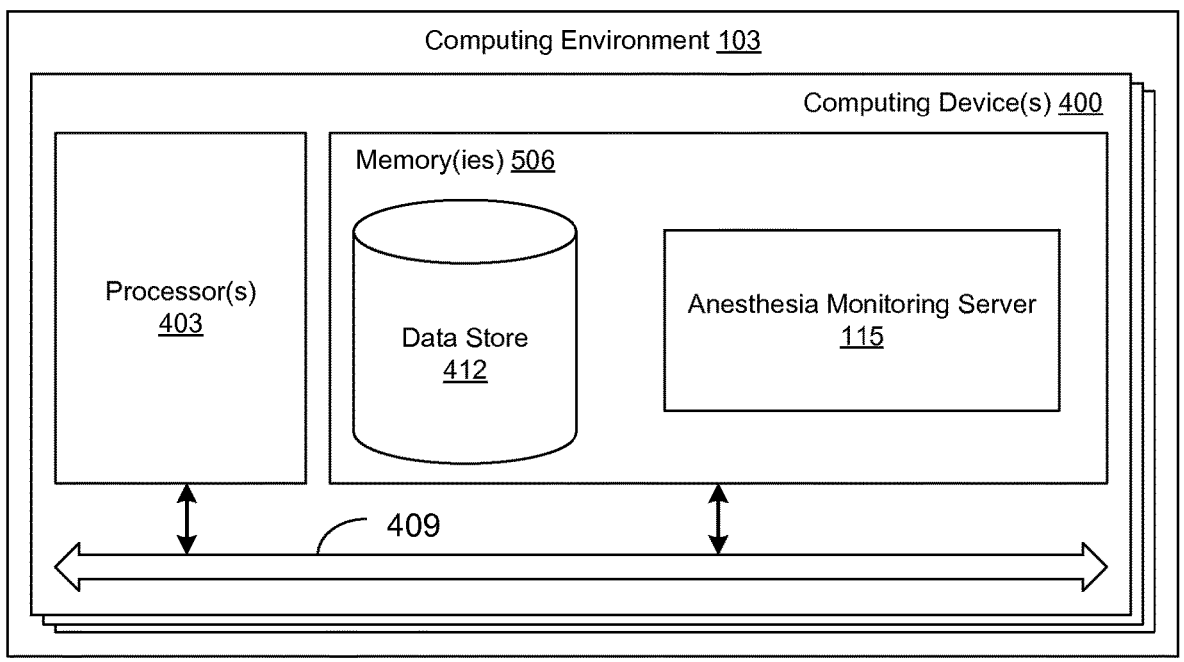
FIG. 4 is a schematic block diagram that provides one example illustration of a computing environment employed in the networked environment of FIG. 1 according to various embodiments of the present disclosure.

With reference to FIG. 4, shown is a schematic block diagram of the computing environment 103 according to an embodiment of the present disclosure. The computing environment 103 includes one or more computing devices 400. Each computing device 400 includes at least one processor circuit, for example, having a processor 403 and a memory 406, both of which are coupled to a local interface 409. To this end, each computing device 400 may comprise, for example, at least one server computer or like device. The local interface 409 may comprise, for example, a data bus with an accompanying address/control bus or other bus structure as can be appreciated.

Stored in the memory 406 are both data and several components that are executable by the processor 403. In particular, stored in the memory 406 and executable by the processor is the anesthesia monitoring server 115 and potentially other applications. Also stored in the memory 406 may be a data store 412 and other data. In addition, an operating system may be stored in the memory 406 and executable by the processor 403.

It is understood that there may be other applications that are stored in the memory 406 and are executable by the processor 403 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 406 and are executable by the processor 403. In this respect, the term "executable" means a program file that is in a form that can ultimately be run by the processor 403. Examples of executable programs may be, for example, a compiled program that can be translated into machine code in a format that can be loaded into a random access portion of the memory 406 and run by the processor 403, source code that may be expressed in proper format such as object code that is capable of being loaded into a random access portion of the memory 406 and executed by the processor 403, or source code that may be interpreted by another executable program to generate instructions in a random access portion of the memory 406 to be executed by the processor 403, etc. An executable program may be stored in any portion or component of the memory 406 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 406 is defined herein as including both volatile and nonvolatile memory and data storage components. Volatile components are those that do not retain data values upon loss of power. Nonvolatile components are those that retain data upon a loss of power. Thus, the memory 406 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 403 may represent multiple processors 403 and/or multiple processor cores and the memory 406 may represent multiple memories 406 that operate in parallel processing circuits, respectively. In such a case, the local interface 409 may be an appropriate network that facilitates communication between any two of the multiple processors 403, between any processor 403 and any of the memories 406, or between any two of the memories 406, etc. The local interface 409 may comprise additional systems designed to coordinate this communication, including, for example, performing load balancing. The processor 403 may be of electrical or of some other available construction.

Although the anesthesia monitoring interface 121 (FIG. 1), the anesthesia monitoring server 115, the anesthesia monitoring remote client 127 (FIG. 1), and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowchart of FIG. 3 shows the functionality and operation of an implementation of portions of the networked environment 100 (FIG. 1). If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 403 in a computer system or other system. The machine code may be converted from the source code, etc. If embodied in hardware, each block may represent a circuit or a number of interconnected circuits to implement the specified logical function(s).

Although the flowchart of FIG. 3 shows a specific order of execution, it is understood that the order of execution may differ from that which is depicted. For example, the order of execution of two or more blocks may be scrambled relative to the order shown. Also, two or more blocks shown in succession in FIG. 3 may be executed concurrently or with partial concurrence. Further, in some embodiments, one or more of the blocks shown in FIG. 3 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the anesthesia monitoring interface 121, the anesthesia monitoring server 115, and the anesthesia monitoring remote client 127, that comprises software or code can be embodied in any non-transitory computer-readable medium for use by or in connection with an instruction execution system such as, for example, a processor 403 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the anesthesia monitoring interface 121, the anesthesia monitoring server 115, and the anesthesia monitoring remote client 127, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 400, or in multiple computing devices in the same computing environment 103. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The present disclosure may be described by at least the following clauses:

1. A non-transitory computer-readable medium embodying a program executable in at least one computing device, comprising: code that receives vital signs for a plurality of patients in a plurality of operating rooms of a medical facility, individual ones of the patients undergoing anesthesia; code that generates a first user interface facilitating a user selection of one of the patients or one of the operating rooms; and code that generates a second user interface encoding a plurality of vital signs for a corresponding one of the patients in response to the user selection.

2. A system, comprising: a mobile computing device; and an anesthesia monitoring remote client executed by the mobile computing device, the anesthesia monitoring remote client comprising: logic that renders, upon a display, a selectable listing of a plurality of operating rooms; logic that requests, from another computing device, current status information for a patient associated with a selected one of the operating rooms and undergoing anesthesia; and logic that renders, upon the display, a plurality of vital signs for the patient undergoing anesthesia in response to receiving the current status information.

3. The system of clause 2, wherein the current status information includes an image of operating room equipment that displays at least one of the vital signs.

4. The system of clauses 2 to 3, wherein the anesthesia monitoring remote client further comprises logic that generates an alert based at least in part on time remaining until a scheduled regulatory compliance check upon the anesthesia of the patient.

5. The system of clauses 2 to 4, wherein the anesthesia monitoring remote client further comprises logic that authenticates a physician user based at least in part on at least one security credential provided by the physician user.

6. The system of clauses 2 to 5, wherein the anesthesia monitoring remote client further comprises logic that generates an alarm in response to determining that at least one of the vital signs meets an alarm threshold.

7. The system of clauses 2 to 6, wherein the anesthesia monitoring remote client further comprises logic that renders, upon the display, a user interface configured to facilitate reassignment of the patient to another physician.

8. The system of clauses 2 to 7, wherein the anesthesia monitoring remote client further comprises logic that renders, upon the display, a user interface that facilitates establishing at least one alarm threshold for individual ones of the vital signs.

9. The system of clauses 2 to 8, wherein the anesthesia monitoring remote client further comprises logic that renders, upon the display, pediatric anesthesia dosing for the patient in response to determining that a weight of the patient meets a pediatric weight threshold.

10. The system of clauses 2 to 9, wherein the anesthesia monitoring remote client further comprises logic that renders, upon the display, a graphical indication of time remaining until a next scheduled anesthesia compliance check for the patient.

11. The system of clauses 2 to 10, wherein the anesthesia monitoring remote client further comprises logic that renders, upon the display, a graphical indication of time elapsed since a previous anesthesia compliance check for the patient.

12. The system of clauses 2 to 11, wherein the anesthesia monitoring remote client further comprises: logic that receives a user selection of a medical history component via the display; and logic that renders, upon the display, medical history information for the patient in response to the user selection.

13. The system of clauses 2 to 12, wherein the anesthesia monitoring remote client further comprises logic that renders, upon the display, a user interface based at least in part on at least one of the vital signs and data describing an advanced cardiac life support (ACLS) protocol.

14. A method, comprising: determining, by a computing device, an anesthesia schedule of a physician, the anesthesia schedule indicating a plurality of patients in a plurality of operating rooms in a medical facility who are to receive anesthesia administered under supervision of the physician; authenticating, by the computing device, the physician at a mobile client; generating, by the computing device, a first user interface that facilitates an operating room selection by the physician, the first user interface generated based at least in part on the anesthesia schedule; and generating, by the computing device, a second user interface that includes a plurality of vital signs for a patient undergoing anesthesia in a particular operating room selected by the physician via the first user interface.

15. The method of clause 14, further comprising generating, by the computing device, a third user interface that includes medical history information of the patient.

16. The method of clauses 14 to 15, further comprising generating, by the computing device, an alert in response to determining that one of the patients is in an assigned one of the operating rooms.

17. The method of clauses 14 to 16, further comprising generating, by the computing device, an alert in response to determining that one of the patients is ready to exit anesthesia.

18. The method of clauses 14 to 17, further comprising generating, by the computing device, an alarm for a plurality of physicians based at least in part on respective locations of corresponding mobile devices of the physicians in response to at least one of the vital signs meeting an alarm threshold.

19. The method of clauses 14 to 18, further comprising acquiring, by the computing device, at least one of the vital signs based at least in part on an image captured from the particular operating room.

20. The method of clauses 14 to 19, further comprising facilitating, by the computing device, transfer of the patient and the particular operating room by the physician to a second anesthesia schedule of a second physician.

21. The method of clauses 14 to 20, further comprising receiving, by the computing device, an indication that a scheduled supervisory check upon the anesthesia has been completed by the physician.

22. The method of clauses 14 to 21, further comprising determining, by the computing device, a time remaining until a next scheduled supervisory check upon the anesthesia by the physician.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A non-transitory computer-readable medium embodying a program executable in at least one computing device, wherein when executed the program causes the at least one computing device to at least:
   receive an image of operating room equipment;
   receive vital signs for a plurality of patients in a plurality of operating rooms of a medical facility, individual ones of the patients undergoing anesthesia, wherein at least one of the vital signs is extracted from the image of operating room equipment;
   generate a first user interface facilitating a user selection of one of the patients or one of the operating rooms using corresponding user interface components for each of the patients or each of the operating rooms;
   generate a second user interface encoding a plurality of vital signs for a corresponding one of the patients in response to the user selection, wherein the second user interface includes at least one user-selectable component that adjusts at least one alarm threshold for individual ones of the vital signs on a per-patient basis;
   determine that at least one of the vital signs meets a particular alarm threshold configured through the second user interface;
   determine respective locations of a plurality of provider mobile computing devices; and
   generate an alarm via at least one of the provider mobile computing devices based at least in part on determining from the respective locations of the provider mobile computing devices that the at least one of the provider mobile computing devices is nearest to a corresponding one of the patients and in response to the at least one of the vital signs of the corresponding one of the patients meeting the particular alarm threshold.

2. The non-transitory computer-readable medium of claim 1, wherein the at least one user-selectable component comprises a slider.

3. A system, comprising:
   a mobile computing device; and
   an anesthesia monitoring remote client executable by the mobile computing device, wherein when executed the anesthesia monitoring remote client causes the mobile computing device to at least:
      render, upon a display, a selectable listing of a plurality of operating rooms, the selectable listing including corresponding user interface components for each of the operating rooms;
      receiving a user selection of one of the corresponding user interface components corresponding to a particular operating room;
      request, from another computing device, current status information for a patient associated with the particular operating room and undergoing anesthesia;
      render, upon the display, a plurality of vital signs for the patient undergoing anesthesia in response to receiving the current status information;
      determine a current location of the mobile computing device;
      generate an alarm in response to determining that at least one of the vital signs meets an alarm threshold and based at least in part on the current location of the mobile computing device; and
      render, upon the display, a user interface that includes at least one user-selectable component that adjusts at least one alarm threshold for individual ones of the vital signs on a per-patient basis.

4. The system of claim 3, wherein the current status information includes an image of operating room equipment that displays at least one of the vital signs.

5. The system of claim 3, wherein when executed the anesthesia monitoring remote client further causes the mobile computing device to at least generate an alert based at least in part on time remaining until a scheduled regulatory compliance check upon the anesthesia of the patient.

6. The system of claim 3, wherein when executed the anesthesia monitoring remote client further causes the mobile computing device to at least authenticate a physician user based at least in part on at least one security credential provided by the physician user.

7. The system of claim 3, wherein when executed the anesthesia monitoring remote client further causes the mobile computing device to at least render, upon the display, another user interface configured to facilitate reassignment of the patient to another physician.

8. The system of claim 3, wherein when executed the anesthesia monitoring remote client further causes the mobile computing device to at least render, upon the display, pediatric anesthesia dosing for the patient in response to determining that a weight of the patient meets a pediatric weight threshold.

9. The system of claim 3, wherein when executed the anesthesia monitoring remote client further causes the mobile computing device to at least render, upon the display, a graphical indication of time remaining until a next scheduled anesthesia compliance check for the patient or a graphical indication of time elapsed since a previous anesthesia compliance check for the patient.

10. The system of claim 3, wherein when executed the anesthesia monitoring remote client further causes the mobile computing device to at least:
receive a user selection of a medical history component via the display; and
render, upon the display, medical history information for the patient in response to the user selection.

11. The system of claim 3, wherein when executed the anesthesia monitoring remote client further causes the mobile computing device to at least render, upon the display, another user interface based at least in part on at least one of the vital signs and data describing an advanced cardiac life support (ACLS) protocol.

12. The system of claim 3, wherein when executed the anesthesia monitoring remote client further causes the mobile computing device to at least perform a pairing function to pair the anesthesia monitoring remote client with an operating room computing device in the selected one of the operating rooms when the mobile computing device is in close proximity to the operating room computing device.

13. The system of claim 3, wherein when executed the anesthesia monitoring remote client further causes the mobile computing device to at least:
automatically determine a location of the mobile computing device; and
automatically determine the plurality of operating rooms based at least in part on the location of the mobile computing device.

14. A method, comprising:
determining, by a computing device, an anesthesia schedule of a physician, the anesthesia schedule indicating a plurality of patients in a plurality of operating rooms in a medical facility who are to receive anesthesia administered under supervision of the physician;
authenticating, by the computing device, the physician at a first mobile client;
generating, by the computing device, a first user interface on the first mobile client that facilitates an operating room selection by the physician from among the operating rooms, the first user interface generated based at least in part on the anesthesia schedule and including corresponding user interface components for each of the operating rooms;
generating, by the computing device, a second user interface on the first mobile client that includes a plurality of vital signs for a patient undergoing anesthesia in a particular operating room selected by the physician via the first user interface, wherein the second user interface includes at least one user-selectable component that adjusts at least one alarm threshold for individual ones of the vital signs on a per-patient basis; and
facilitating, by the computing device, transfer of the patient and the particular operating room by the physician via the first mobile client to a second anesthesia schedule of a second physician accessible via a second mobile client.

15. The method of claim 14, further comprising:
generating, by the computing device, a first alert in response to determining that one of the patients is in an assigned one of the operating rooms; and
generating, by the computing device, a second alert in response to determining that the one of the patients is ready to exit anesthesia.

16. The method of claim 14, further comprising generating, by the computing device, an alarm for a plurality of physicians based at least in part on respective locations of corresponding mobile devices of the physicians in response to at least one of the vital signs meeting an alarm threshold.

17. The method of claim 14, further comprising extracting, by the computing device, at least one of the vital signs from an image of operating room equipment.

18. The method of claim 14, further comprising receiving, by the computing device, an indication that a scheduled supervisory check upon the anesthesia has been completed by the physician.

19. The method of claim 14, further comprising determining, by the computing device, a time remaining until a next scheduled supervisory check upon the anesthesia by the physician.

20. The method of claim 14, wherein the corresponding user interface components are distinctively color coded for each of the operating rooms.

* * * * *